United States Patent
Barski et al.

(10) Patent No.: US 6,269,176 B1
(45) Date of Patent: Jul. 31, 2001

(54) METHOD FOR X-RAY ANTISCATTER GRID DETECTION AND SUPPRESSION IN DIGITAL RADIOGRAPHY

(75) Inventors: Lori L. Barski, Mendon; Xiaohui Wang, Rochester, both of NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/218,136

(22) Filed: Dec. 21, 1998

(51) Int. Cl.[7] .................................................. G06K 9/00
(52) U.S. Cl. ............................................. 382/128; 128/922
(58) Field of Search ............................. 128/916; 382/106, 382/132, 128; 364/413.13; 378/98.3

(56) References Cited

U.S. PATENT DOCUMENTS

| | | |
|---|---|---|
| 4,792,900 | 12/1988 | Sones et al. . |
| 4,851,984 * | 7/1989 | Doi et al. ........................ 364/413.23 |
| 5,661,818 | 8/1997 | Gaborski et al. . |
| 5,671,288 * | 9/1997 | Wilhelm et al. ..................... 382/128 |
| 5,764,307 | 6/1998 | Ozcelik et al. . |
| 5,915,036 * | 6/1999 | Grunkin ............................... 382/132 |
| 5,974,159 * | 10/1999 | Lubin et al. ......................... 382/106 |
| 6,012,458 * | 1/2000 | Mo et al. ............................ 128/916 |
| 6,031,892 * | 2/2000 | Karellas .............................. 378/98.3 |

* cited by examiner

Primary Examiner—Joseph Mancuso
Assistant Examiner—Abolfazl Tabatabai
(74) Attorney, Agent, or Firm—William F. Noval (57) ABSTRACT

We demonstrate a comprehensive image processing system to automatically detect the use of a stationary anti-scatter device (also referred to as a linear grid) and suppress the artifacts that such a device creates in a digital radiographic images. The detection process consists of the stages of determining an appropriate region of the image from which to perform the analysis; performing a spectral analysis to identify the grid frequencies; and identifying the most likely grid line frequency. When a grid is detected, the results of the detection process are used to perform adaptive grid suppression using custom designed blurring filters and a plurality of adaptation methods.

28 Claims, 10 Drawing Sheets

Fig. 10 w = (right_bound - left_bound)/8 a: 0 to left_bound + w mapped to 0
b: left_bound + w to left_bound + 2w mapped to 1
c: left_bound + 2w to left_bound + 3w mapped to 2
d: left_bound + 3w to left_bound + 4w mapped to 3
e: left_bound + 4w to left_bound + 5w mapped to 4
f: left_bound + 5w to left_bound + 6w mapped to 5
g: left_bound + 6w to left_bound + 7w mapped to 6
h: left_bound + 7w to 4095 mapped to 7

METHOD FOR X-RAY ANTISCATTER GRID DETECTION AND SUPPRESSION IN DIGITAL RADIOGRAPHY

FIELD OF THE INVENTION

This invention relates to digital medical imaging, particularly the presentation of digital projection radiography images (acquired from a film digitizer, a computed radiography system or a flat panel direct digital detector) for improved image quality.

BACKGROUND OF THE INVENTION

The use of anti-scatter devices such as linear grids has been proven to improve contrast and signal to noise in radiographic images. Because of this, these devices are commonly found in most radiology departments and come in an assortment of configurations. A grid typically consists of a series of lead foil strips separated by xray-transmissive spacers. The spacing of the strips determines the grid frequency, and the height-to-distance between lead strips determines the grid ratio. Grids can be oriented horizontally or vertically. Two general methods of use exist for grids—stationary and moving (Bucky-Potter configuration). Of the moving type grids, the shadows of the lead strips are blurred out by the motion, which can be either reciprocating or unidirectional (single stroke). Conversely, stationary grids cause the shadows of the lead strips to be imposed onto the radiographic image. In cases where a moving grid is not reciprocating properly, or the time of exposure is faster than the time it takes for the grid to move, the resulting image will also have the lead strip shadows present.

Due to the migration of the radiology department from analog screen/film to digital imaging and PACS, issues once germane to the radiologist, such as the shadows of grid lines in the film images, are now becoming a source of displeasure and annoyance, particularly when primary diagnosis is being done on soft copy or a CRT. The cause of the problem is the high frequency of the lead strips found in the grids which cause artifacts in the image that resemble moire patterns and can hinder interpretation. The patterns are caused by aliasing which is introduced due to the discrete sampling of the image by the scanning system. Factors which contribute to the aliasing are the grid resolution (grid line frequency), the sampling frequency and the modulation transfer function (MTF) of the image acquisition device. The most typical manifestation of the problem occurs when an image is reduced in size for the purpose of soft copy display on a monitor/CRT at a slightly reduced size.

In order to develop a comprehensive solution to deal with the aliasing artifact, one must first detect if a stationary grid is present in the image. The use of stationary grids in most radiography departments, although not random, is sporadic. And because the most commonly used grid configuration, the moving Bucky-Potter, can experience malfunction, prediction based upon exam information can be erroneous. Therefore, an image analysis technique is required to automatically detect the presence or absence of a grid in every image. U.S. Pat. No. 5,661,818, issued Aug. 26, 1997, inventors Gaborski et. al., developed a grid detection method which bases its detection decision on a double auto-correlation calculation. Variances are measured independently, both horizontally and vertically and a statistical F test is performed to determine if the variances are the same over a randomly chosen sampling of locations within the image. Votes are then tallied and if a majority exists that the variances are different, a decision is made in favor of a grid being present. However, this method is limited because it does not provide any characteristic information about the nature of the grid if one is detected—the grid line frequency (s), the noise power of the grid, etc. Such information is critical to the second stage of an automated solution to deal with grid aliasing—that of suppressing the grid lines.

Once a grid is detected, the presence of the grid shadows needs to be either removed or suppressed. These shadows can be considered a form of noise and in the field of digital image processing, this type of noise artifact is referred to as correlated noise. Well known methods exist to characterize and eliminate correlated noise (see "Noise Cleaning", W. K. Pratt, *Digital Image Processing*, $2^{nd}$ Edition, John Wiley & Sons, Inc., 1991). However, the frequency of grid lines within a given device are quite variable. This is due to the manual nature of the manufacturing process. Because of this, 2-D Fourier filtering methods involving the use of a bandstop filters are less straight forward and are prone to the introduction of artifacts if the filter is incorrectly designed. Also, commercial viability of such methods requires special purpose hardware due to the relatively large format of the image (2K×2K up to 4K×4K, 12 bits/pixel) in order to meet near real-time speed requirements. Spatial filtering is the next best choice, such as convolution with a blurring filter. But, such a solution results in a global reduction of image detail if applied indiscriminately. Adaptive filtering methods are therefore appropriate.

U.S. Pat. No. 4,792,900, issued 1988, inventors Sones et al., describe a method of adaptive noise suppression used in dual energy digital radiography. Both low and high energy images are filtered in two dimensions, based upon the pixel value of the respective images using either bone specific or soft tissue specific filter functions which are of a predefined size (filter support not dependent upon noise being suppressed). Although the method taught by Sones, et. al. does somewhat utilize custom filter functions as a function of signal level, the method is not designing the filters as a function of the noise which it is trying to suppress, nor are the filters gaussian in shape. Not adapting the filter size on an image by image basis in order to meet the noise blurring objective is a significant deficiency, as it is in U.S. Pat. No. 5,764,307, issued 1998, inventors Ozcelik, et. al. Ozcelik et. al. describe a method for spatially adaptive filtering for video encoding where the displaced frame difference (DFD), i.e. the temporal difference between 2 consecutive frames, is blurred to reduce compression artifacts. This approach also uses a 2-D fixed filter support (size). In the present invention, such 2-D filtering methods would be too indiscriminate because of the 1-D orientation of the grid shadows. Thus the present invention enjoys the benefits of custom filter design on an image-by-image basis, faster processing and the preservation of detail in the orientation corresponding to the orientation of the grid.

In accordance with the present invention, there is provided a new and comprehensive image processing system which overcomes the above referenced problems.

SUMMARY OF THE INVENTION

The present invention provides an automatic method to quickly detect and suppress grid lines in projection radiographic images. More specifically, the grid detection method includes a means for detecting if a grid is present, and if present, determining what the characteristics of the grid are in terms of the frequency of the grid, the magnitude (in terms of 1D Fourier spectra) of the grid peak, the spread of the grid peak (in terms of the half-width of full maximum of the grid peak), the total energy of the grid peak, the orientation of the grid, and a figure-of-merit assessing the confidence of the detection. The grid suppression method includes a means for building a series of one dimensional gaussian blur filters based upon the grid characteristics and a means for adaptively applying the filters. A plurality of methods to adaptively apply the filters is described.

ADVANTAGEOUS EFFECT OF THE INVENTION

The present invention has the following advantages:

1. The combined grid detection and suppression methods solve the problem of moire artifacts caused by grid aliasing in digital projection radiographic images. No other prior art was found which does so.
2. The grid detection method both determines if a grid is used, and if so, what the characteristics of the grid are such as grid frequency, magnitude, energy, the spread of the grid peak, the orientation of the grid, and a figure-of-merit for the confidence of the detection.
3. The grid suppression method automatically builds custom designed 1-D filters to enable blurring of the grid shadows.
4. The grid suppression method can adaptively apply the custom designed 1-D filters to minimize indiscriminate suppression of image detail based upon pixel value.
5. The grid suppression method can adaptively apply the custom designed 1-D filters to minimize indiscriminate suppression of image detail based upon both pixel value and image activity jointly.
6. The grid suppression method can iteratively apply the custom designed 1-D filters in a controlled fashion, using the grid detection method as a feed-back mechanism to drive the degree of blur.

DETAILED DESCRIPTION OF THE INVENTION

The method of the present invention is described as a series of operations performed on a digital image, such as a digital radiographic image of a body part. The digital image can be formed by the digital image acquisition system of FIG. 4. As shown, x-ray source 200 projects x-rays through object 202 (such as a body part extremity, e.g., hand or foot) to image acquisition system 204. The image acquisition system can be, for example, (1) a standard x-ray screen/film combination which produces an x-ray film image which is processed chemically or thermally and the processed film digitized by a scanner/digitizer 206; (2) a computed radiography system where a latent x-ray image is formed in a storage phosphor 204 and a corresponding digital image is produced by reading out the storage phosphor by a CR reader 206; (3) a diagnostic scanner (such as MRI, CT, US, PET) produces an electronic x-ray image which is digitized; and (4) a direct digital acquisition system typically consisting of a phosphor based scintillating screen coupled to an imager (CCD, MOS) through a lens or fiber optic system.

Figure 5:
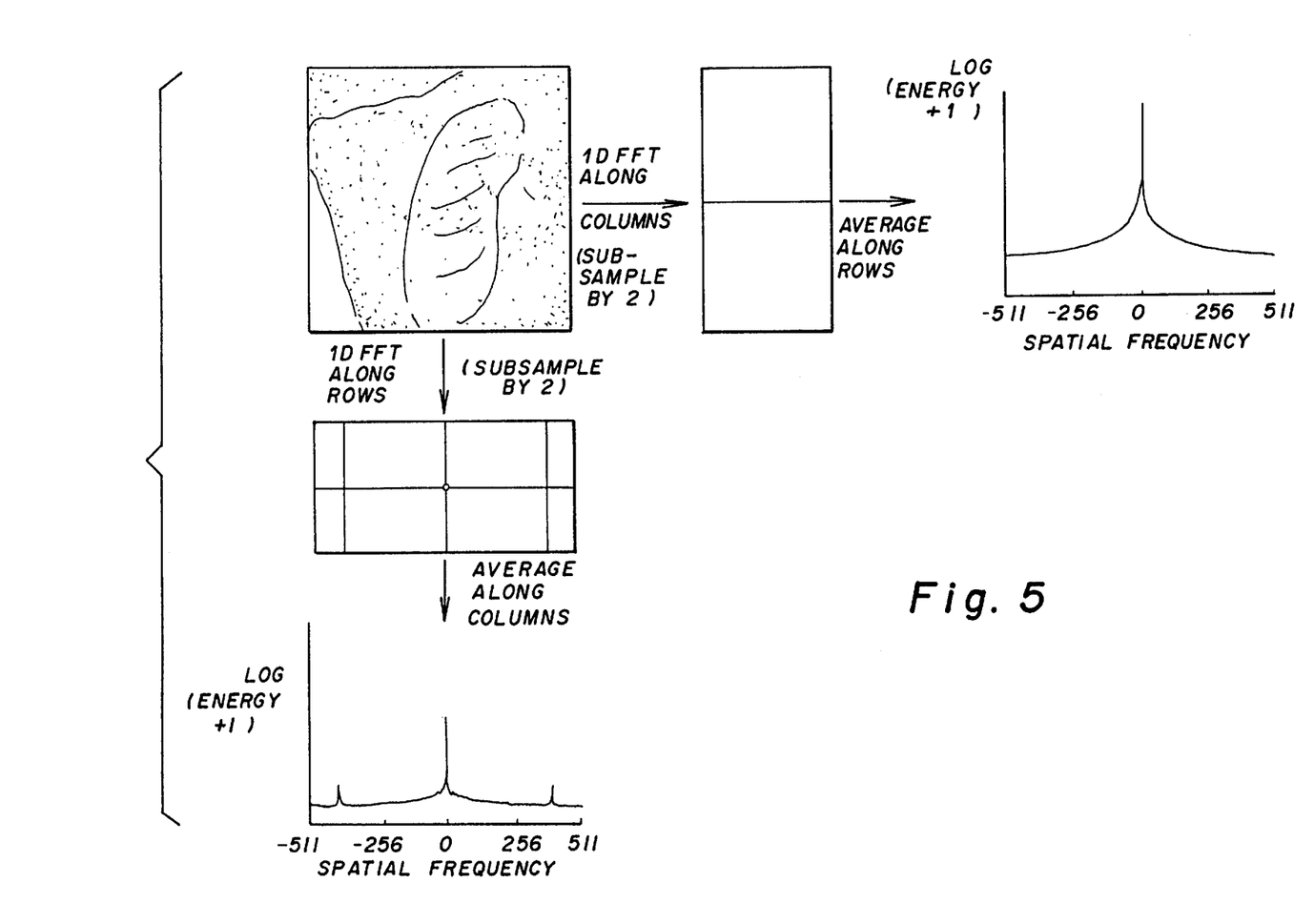
FIG. 5 is a diagram illustrating the process of 1D FFT Power spectrum analysis.

The digital image is processed in image processor 208, according to the method of the present invention. Image processor 208 can take the form of a digital computer, such as illustrated in FIG. 5. In such case, one or more of the steps of said method can be carried out using software routines. Image processor 208 can also include hardware or firmware for carrying out one or more of said method steps. Thus, the steps of the method of the invention can be carried out using software, firmware, and hardware, either alone or in any preferable combination.

As shown in FIG. 5, a digital computer 300 includes a memory 310 for storing digital images, application programs, operating system, etc. Memory 310 can include mass memory (such as a hard magnetic disc or CD ROM), and fast memory (such as RAM). Computer 300 also includes input device 312 (such as a keyboard, mouse, touch screen), display 314 (CRT monitor, LCD), central processing unit 316 (microprocessor), output device 318 (thermal printer, dot matrix printer, laser printer, ink jet printer). Components 310,312,314,316,318 are connected together by control/data bus 320. Computer 300 can include a transportable storage medium drive 322 for reading from and/or writing to transportable storage media 324, such as a floppy magnetic disk or writeable optical compact disk (CD).

As used in this application, computer readable storage medium can include, specifically, memory 310 and transportable storage medium 324. More generally, computer storage medium may comprise, for example, magnetic storage media, such as magnetic disk (hard drive, floppy disk) or magnetic tape; optical storage media, such as optical disk, optical tape, or machine readable bar code; solid state electronic storage devices, such as random access memory (RAM), read only memory (ROM); or any other physical device or medium which can be employed to store a computer program.

Figure 1:
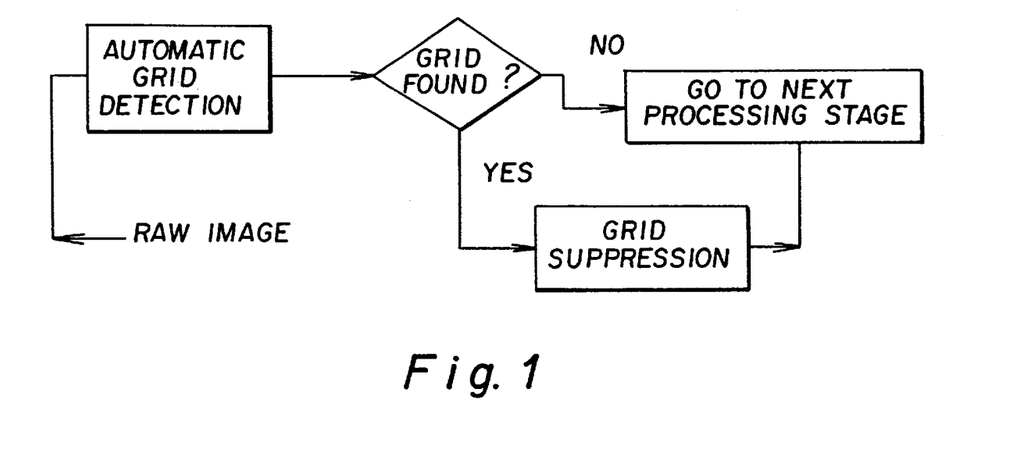
FIG. 1 is a block diagram of the comprehensive system encompassing both the grid detection and grid suppression methods.

The present invention provides a comprehensive image processing system to improve radiographic images which contain stationary grids. FIG. 1 is a block diagram of the stages. Raw image data is first processed by the automatic grid detection algorithm. If a grid is detected, the image is passed to the second stage of grid suppression. After suppression, or if no grid is detected, the image is then passed on in the imaging chain.

Grid Detection

The grid detection algorithm determines whether an antiscatter grid has been used when an image is acquired. It is required that the performance of this stage be fast and robust. This is because (1) every image needs to run through this stage no matter whether there are grid lines or not, a slow response can be the "bottle neck" of the whole algorithm, and (2) a false alarm in the detection may cause undesirable blur from the suppression process, which may make small yet diagnostically important details less apparent in the image. For successful grid suppression processing, many parameters associated with the type of grid used need to be identified, such as grid orientation, frequency, total energy, energy coherence etc.

Figure 2:
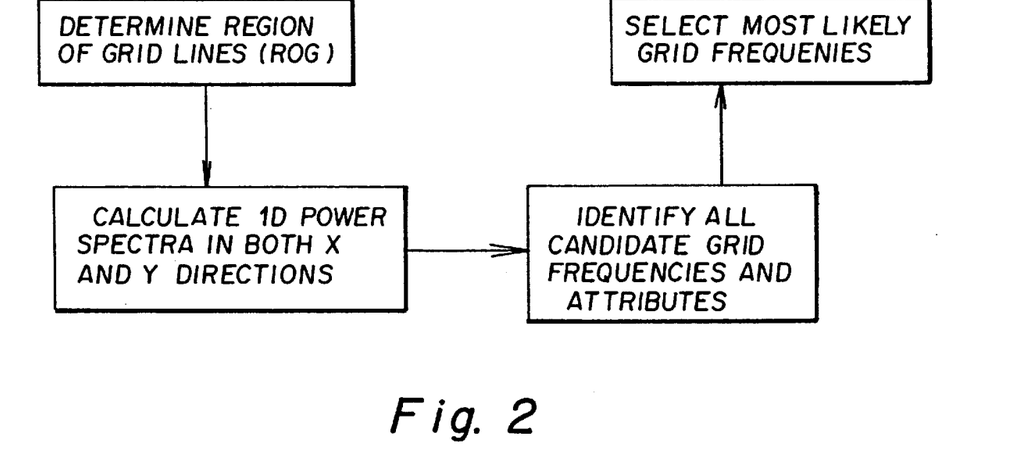
FIG. 2 is a block diagram of the grid detection processing.

Theoretically, the placement of an antiscatter grid can be arbitrary when an image is acquired, therefore the grid lines in the image can be in any orientation. However, based on a prior knowledge of the grids and the process used by the radiographic technologists to take the exposures, grid lines within the image are usually approximately parallel to either the x axis (vertical direction) or the y axis (horizontal direction). For this reason, only one-dimensional (1D) grid detection and suppression in the corresponding orientation are necessary. Even in case the grid lines are not parallel to either the x axis or the y axis, there must exist one dominant orientation between the x and y directions, in which the grid frequency is measured higher, and 1D grid suppression in this dominant orientation can substantially reduce the magnitude of the grid lines. Therefore, 1D grid detections are conducted along both the x and y axes of the image, then only the dominant grid orientation is chosen for the suppression process. As seen in FIG. 2, the detection process is composed of four steps: (1) determination of the image region for analysis, also referred to as the region of grid lines (ROG) (2) obtaining two 1D power (energy) spectra, one in x direction and the other in y direction, (3) identification of all the candidate grid frequencies and their associated parameters, and (4) recognition of the most likely grid frequencies. The four steps are described as follows.

First, a region of the image is selected for grid detection. This selection process depends on many factors, such as image size, detection threshold, accuracy, speed and image representation etc. Because the detection method is based upon the frequency spectra in the image, the well known fast Fourier transform (FFT) technique (W. H. Press, et al, Numerical Recipes in C., Cambridge University Press, 1996) is utilized. The region can be the whole image, and if the image size is not a number of an exact integer power of 2, zero-padding should be used in order to take advantage of the FET method for spectral analysis. For example, an image of 2,048×2,500 pixels should be padded with 2,048×1,596 zeros to create an image of 2,048×4,096 pixels. However taking the whole image for analysis is computationally expensive and usually unnecessary. When the grid lines are so strong in an image that their presence becomes quite objectionable, the spectrum of a small image region can be enough to reliably identify the grid frequency. For this reason, a small and very active region of grid lines (ROG) is extracted from the image for spectral analysis. The size of ROG is derived from the compromise of computation efficiency and frequency resolution; a smaller ROG size will improve the efficiency but can lose the detection accuracy, on the other hand, a larger ROG reduces computation efficiency but improves frequency resolution. In practice, a square ROG of an integer number of 2 pixels, such as 1,024×1,024 is usually chosen.

Figure 3A:
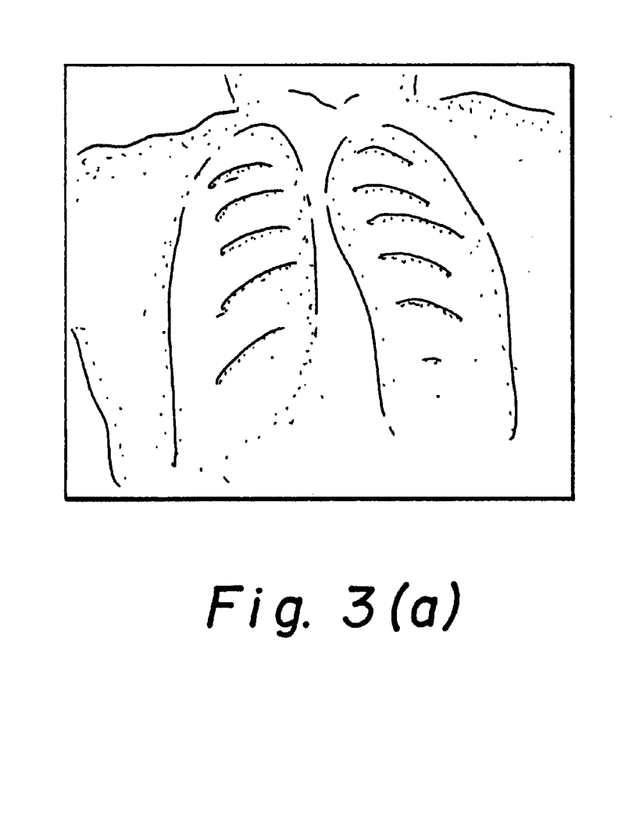
FIG. 3 is a diagram illustrating the process of selecting the most active region of grid lines (ROG).
Figure 3B:
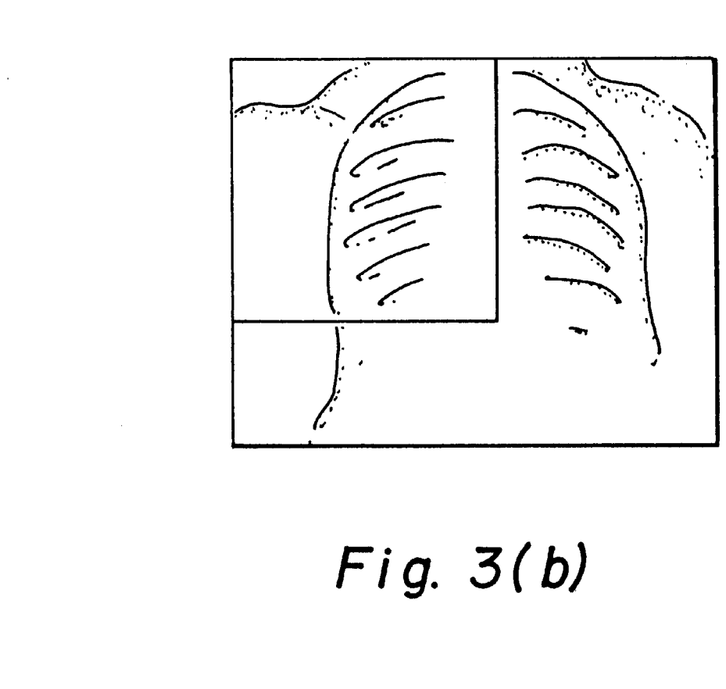

Determination of the most active ROG is based on the image formation process. For example, the intensity of grid lines in a CR image are stronger in the regions where there are less scattered x-rays, i.e., the more direct exposure regions. Ideally these regions can be recognized and used to compose the most active ROG. However such process may be sophisticated if a robust performance is required. A preferred way of determining the most active ROG is to use the regional average of pixel intensities. Since the more direct exposure regions are composed of pixels of either higher or lower intensities depending on the image polarity, a survey of the averaged intensity of all the pixels inside each ROG within the image will determine the most active ROG. The original image can be used for this survey process, however, to improve the computation efficiency, both the image and the ROG are sub-sampled to a smaller size and calculation is conducted using the sub-sampled image. After the intensity average of the pixels within each ROG is obtained, the ROG with the minimum average is selected for white-bone images, or the ROG with the maximum average is selected for black-bone images. The selected ROG is passed to the next step of the detection stage for FFr spectral analysis. Since there are often some pixels in the close proximity of the image boundaries which are not directly related to x-ray image formation, such as the serial number of the phosphor screen for CR images or the information texts, these pixels are excluded from the searching process. An example for the most active ROG selection is shown in FIG. 3.

Second, FFT is conducted and two 1D power spectra are obtained for the selected most active ROG or the zero-padded whole image if one selects to do so. The two 1D power spectra correspond to the energy of the grid lines in the x direction and the y direction, respectively. There are several preferred approaches in obtaining the power spectrum and they are described as follows.

Figure 4:
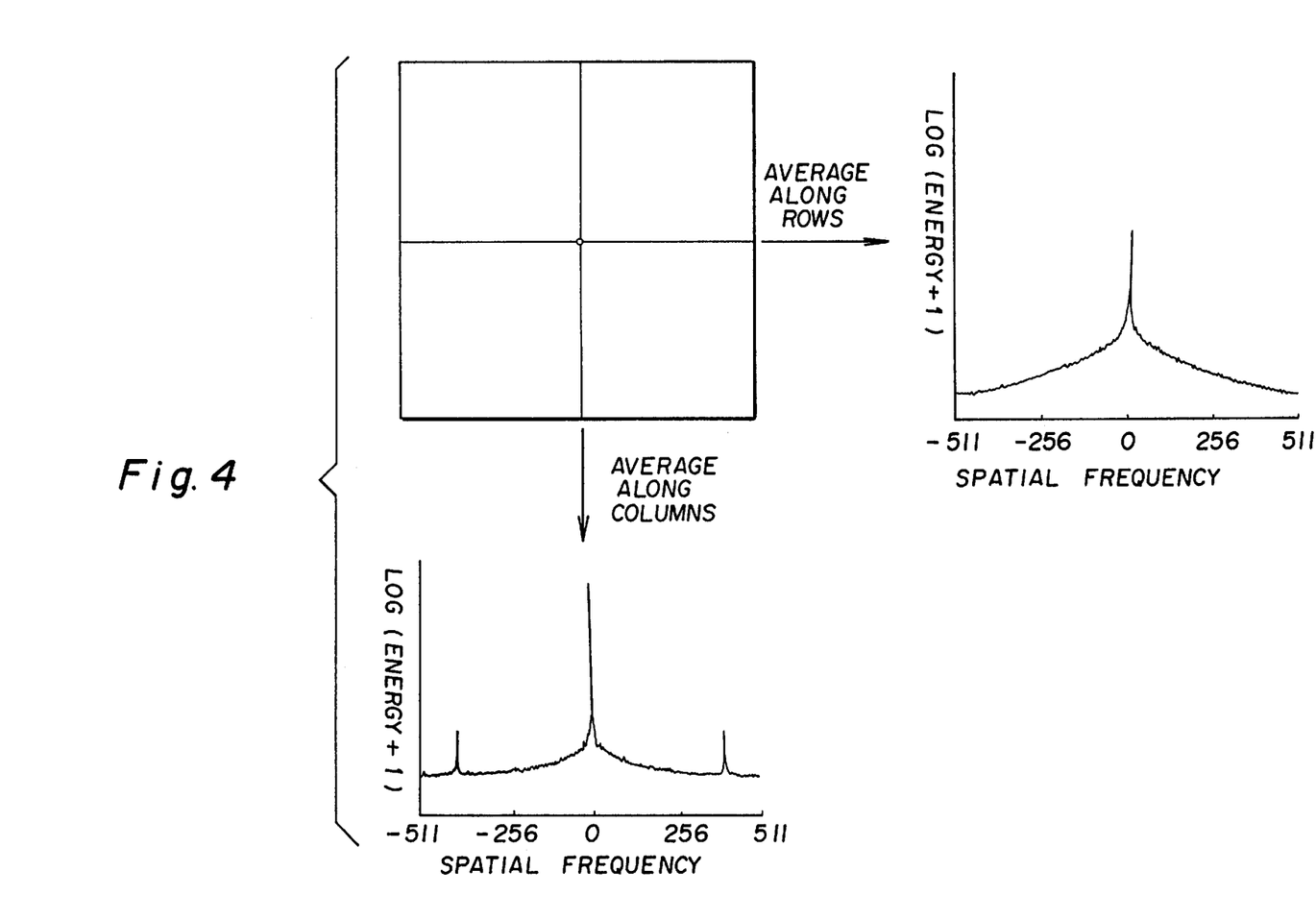
FIG. 4 is a diagram illustrating the process of 2D FFT Power spectrum analysis.

The first approach takes two-dimensional (2D) FFT followed by calculation of the magnitude square of the transform for energy spectra. Since the grid lines in the image are parallel to each other, a very strong coherent grid energy in term of line(s) can be observed in the 2D power spectrum (FIG. 4). Two profiles are readily available by averaging the 2D spectrum along the rows and the columns, respectively. This average process is essentially an evidence accumulation process, it also reduces noise and therefore provides a more robust measure of the grid frequency(s). In the normal situation, the grid lines are parallel to either the x axis or the y axis, therefore the line(s) corresponding to the grid frequency(s) in the power spectrum is also parallel to one of the axis. In this case, one of the two averaged 1D profiles can provide all the information regarding the grid characteristics. However, if the grid lines are not parallel to either the x axis or the y axis, the line(s) in the power spectrum will not be parallel to either axis, in this case the grid characteristics can be obtained using the second approach.

The second approach to obtain power spectra utilizes only 1D FFT. The first approach suffers a compromise between frequency resolution and computation speed. To reliably identify the peak locations in the power spectra, the size of the input image (most active ROG) should be reasonably large, however, a large image size needs more expensive 2D FFT calculation. Based on the actual situation, the second approach only takes the 1D FFT of some line samples in both the x direction and the y direction. Then all the 1D power spectra of each sampled line are averaged in either direction separately. Again this is a evidence accumulation process and it can improve the detection robustness. FIG. 5 shows how the second approach is conducted. The sampling can take every 1, 2, 3, and so on rows (columns) of the image.

Figure 6A:
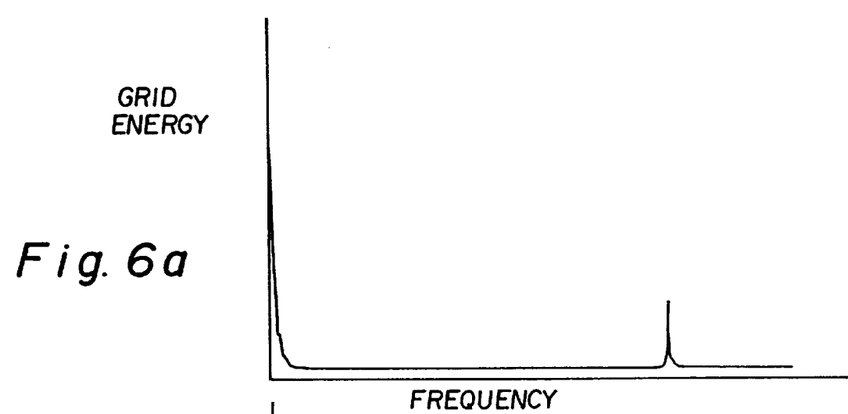
FIG. 6 is a diagram illustrating the process of searching for peaks using morphological processing.
Figure 6B:
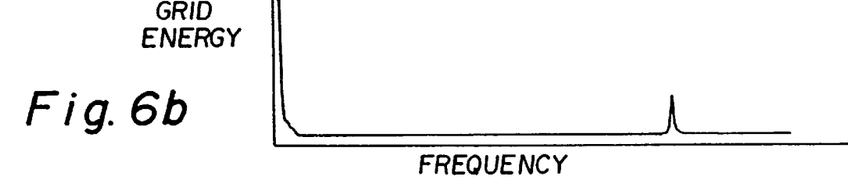
Figure 6C:
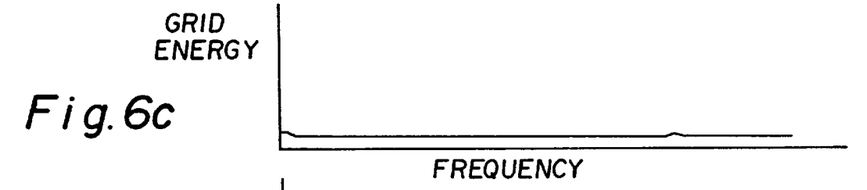
Figure 6D:
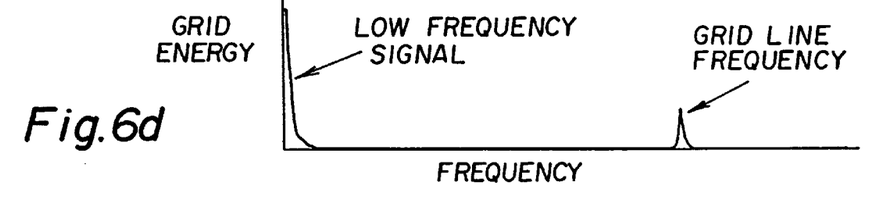

The third step of the grid detection process utilizes a search method to find all the candidate peaks and their associated parameters from the two averaged 1D power spectra. For this purpose, some pre-processing is necessary. Since the pixel intensities of the input image are real numbers, the negative half of FFT is simply the complex conjugate of the positive half, therefore the power spectra are symmetric about its center. This allows only the positive half to be used for the subsequent steps without losing any information (FIG. 6(a)). To reduce the noise, a one dimensional gaussian convolution kernel is applied for spectrum smoothing (FIG. 6(b)). For a robust peak detection and peak energy calculation, the low-frequency background needs to be identified and subtracted from the smoothed spectra. A preferred way of doing this is to use a morphological opening filter with a circular kernel (FIG. 6(c)). The size of the circular kernel should be several times larger than the widest peak width in order to minimize the error of energy calculation. FIG. 6(d) shows one of the processed spectrum. It is quite apparent that all the peaks are isolated and anywhere else is zero in the spectrum. For both gaussian smoothing and morphological operations, mirroring of the data points at the two ends of the 1D spectra is used since the spectra themselves are periodic.

Figure 7:
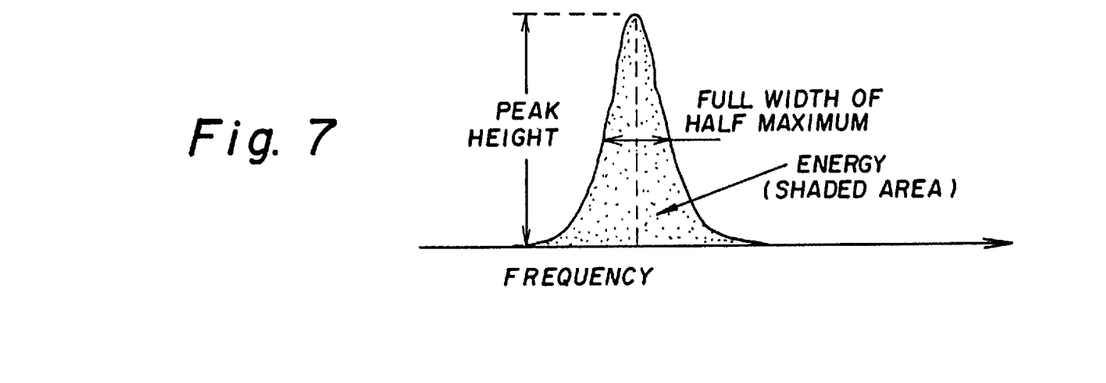
FIG. 7 is a diagram illustrating the various characteristic measurements of the grid detection process.

After all the pre-processing is completed, a search for all the local peaks greater than a predetermined magnitude in the spectra is conducted for the purpose of skipping peaks at very low frequency. Many parameters related to the characteristics of the peaks are therefore calculated. FIG. 7 illustrates these characteristics such as peak location (frequency), peak magnitude, half width of full maximum, total energy, grid orientation and so on. These candidate peaks are sorted based on their energy, and only a predetermined number of peaks with higher energies in each power spectra are passed to the next step for analysis.

The fourth step of the grid detection process involves the calculation of figures-of-merit (FOMs) for each peak and the most likely grid frequencies are recognized. These FOMs include fom_ecohr ,fom_freq and fom_tot, etc. The parameter fom_ecohr is a measure of energy coherence, which is define as the energy per unit frequency, i.e.

$$\text{fom\_eochr} = k \times \frac{\text{energy}}{hwfm}, \quad (1)$$

where hwfm is the half width of full maximum (HWFM) of the peak, and k is a normalization factor to limit fom_echhr within the range between 0 and 1. This measure is used to encourage grid lines having better defined (narrow and strong) peaks in the power spectra. The parameter fom_freq is defined as $$\text{fom\_freq} = \frac{\text{frequency}}{\text{maximum\_frequency}}; \quad (2)$$

where maximum_frequency is the maximum frequency of the power spectrum, such as 512 for a power spectrum of 1,024 data points. This measure is used to encourage grids of higher frequency. This is because the grid line frequency (s) is most likely in the higher frequency region. The parameter fom_tot is the weighted sum of fom_ecohr and fom_freq, i.e., $$\text{fom\_tot} = \text{fom\_ecohr} + \text{fom\_freq}. \quad (3)$$

Finally all the candidate grid peaks detected from both 1D spectra are sorted based on their FOMs, and only those peaks that satisfy the following conditions will be treated as valid grid frequencies:

the measure fom_tot must be larger than a predefined threshold, and the energy must be stronger than a predefined threshold. The output of this stage is a list of grid lines, ranking in the order of their fom_tot, together with their energy, full width of half maximum, frequency and orientation.

It should be mentioned here that peak search can also be conducted directly in the 2D FFT space, in which case 2D morphological filter can be used. Since the grid detection process is essentially finding the peak(s) in either the 1D or 2D power spectra, or equivalently, function optimization, one can use many other methods for peak finding instead of using the morphology filter. For example, golden section search, parabolic interpolation based Brent's search, first derivative-based search, downhill simplex method, Powell's method, conjugate gradient method and etc. ("Minimization and Maximization of Functions" in W. H. Press, et al., Numerical Recipes in C., Cambridge University Press, 1996) are all good.

Grid Suppression

Figure 8:
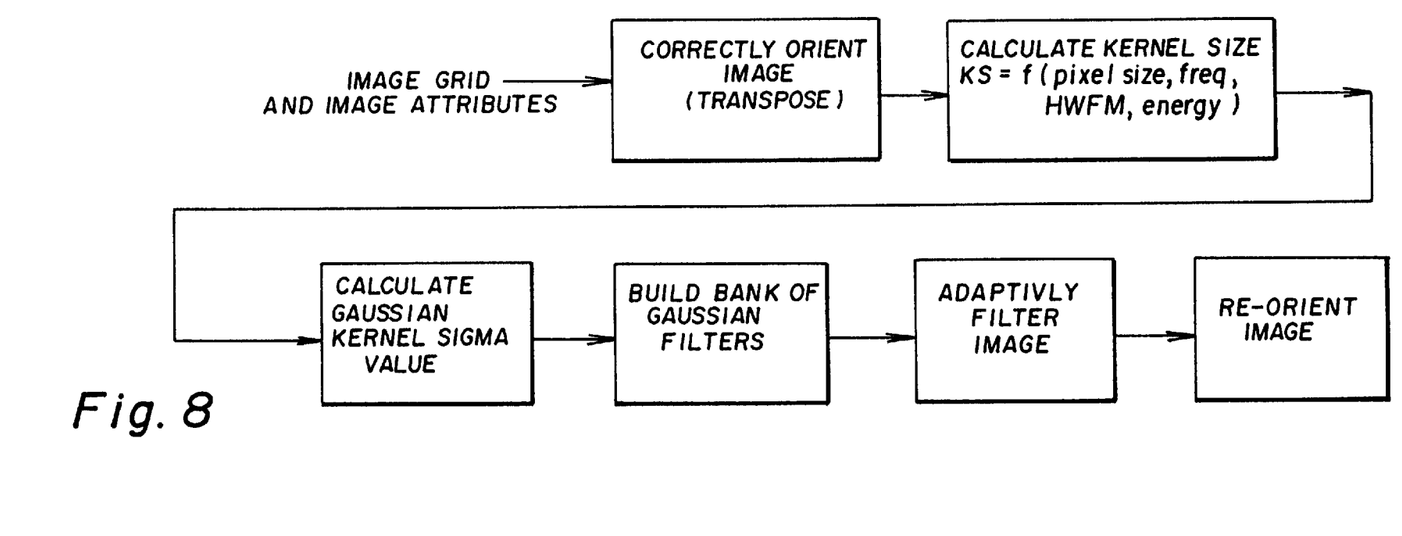
FIG. 8 is a block diagram of the stages of grid suppression processing.

Suppression of the grid lines requires one to balance the tradeoffs between lowering the perception of aliasing (a direct effect of the grid lines), and removing relevant image information due to the suppression process. The present invention utilizes an adaptive blurring process to suppress the grid lines via spatial convolution. Experience from looking at many images containing stationary grids tells us that the perception of the aliasing is lowest in regions of low signal (i.e. where relatively fewer x-rays have penetrated through the patient and exposed the acquisition receptor) and is greatest in regions of medium to higher signal, corresponding to where the contrast of the image is higher. And often coinciding with the low signal regions of the image is the desire to see as much detail as possible. Therefore, the suppression algorithm must do minimal alteration to the original image in low signal regions, and this requirement correlates well with the fact that the grid line shadows are minimally visible. Another factor in determining the degree of suppression required is the energy of the grid. As the grid energy increases, a greater degree of suppression is required. A third factor for the suppression algorithm is the design of the blurring kernels. The kernel needs to be small enough to facilitate fast processing and minimize the blurring of important structures in the image, and large enough to cover the grid line shadow. Therefore, in the preferred embodiment, the strategy for processing is to design appropriate blur kernels (a bank of kernels to be applied adaptively) as a function of pixel size, grid energy, grid frequency and the related span of grid frequencies (the half-width of the full maximum peak). FIG. 8 is a block diagram of the suppression process.

Image Orientation

As shown in FIG. 8, required inputs to the grid suppression process are both the grid and image attributes. The image attributes include things such as the image size and the pixel size. Grid attributes include the orientation of the grid, the frequency, the magnitude, the energy, the half width of full maximum peak, and the grid detection figure of merit. The first step to performing grid suppression is to orient the image so that the grid lines are vertical (the blurring kernels are always horizontal). This stage can be implemented as a simple transpose of the image. An alternative method is to orient the filters to be perpendicular with the orientation of the grid. Both methods are equivalent.

Calculate Kernel Size

Figure 9:
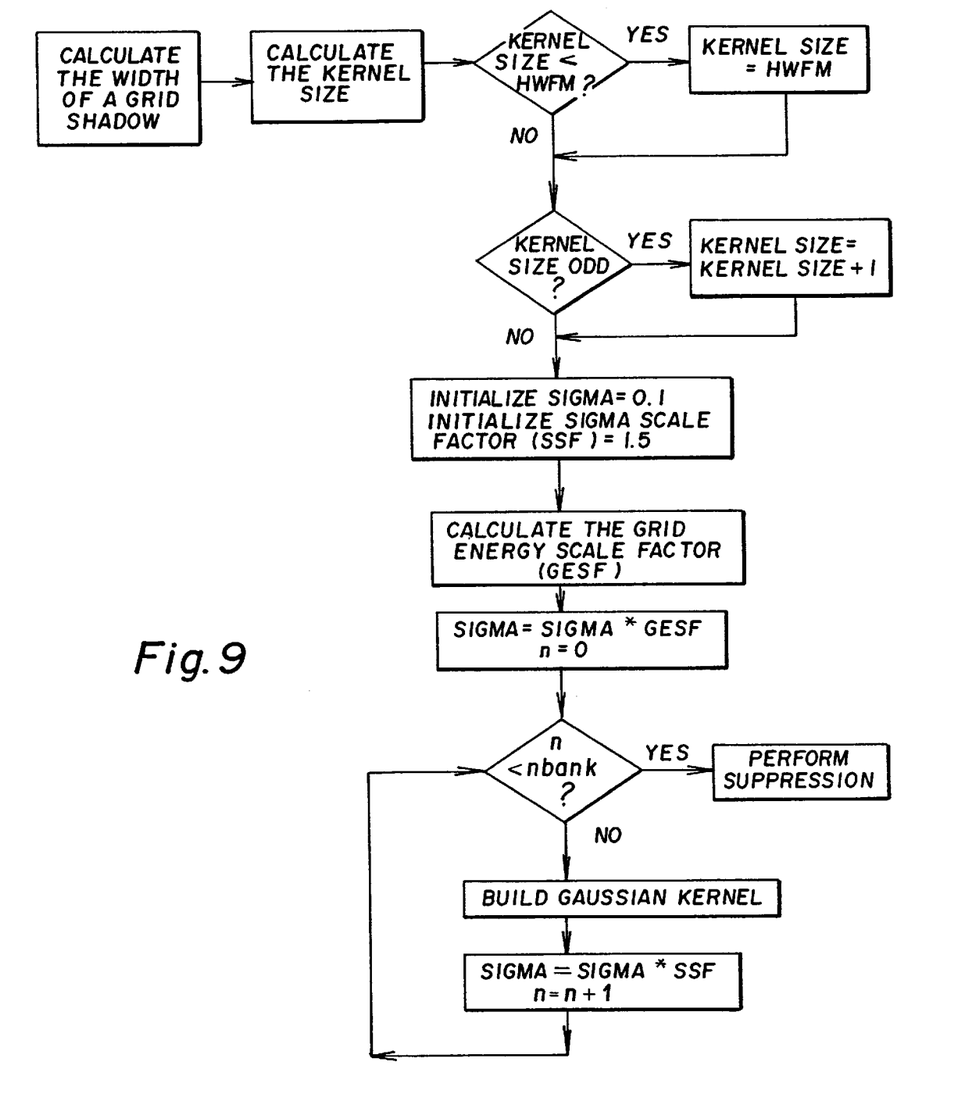
FIG. 9 is a block diagram of the process of 1D gaussian suppression kernels.

Next, the kernel size (to be used for all kernels) is calculated as a function of the image pixel size, the grid frequency, grid energy, and the grid half-width full maximum (HWFM) value. FIG. 9 is a block diagram of the steps used in building the first and all subsequent kernels used in suppression. The width of a grid shadow, grid_width is calculated using:

$$\text{grid\_width} = \frac{nsamples}{2(\text{grid\_frequency})}, \tag{4}$$

where nsamples is the number of points used in calculating the Fourier spectrum (1024 typically) and grid_frequency is the calculated frequency of the grid from the grid detection processing. The kernel size, kernel_size is calculated using:

$$\text{kernel\_size} = \text{grid\_width} \times 3, \tag{5}$$

in order for the kernel to span the grid shadow and both sides. If the kernel size is found to be less than the half width of full maximum (HWFM) of the peak, we set the kernel size to the HWFM value. And if the kernel size is not odd, we decrease the kernel size by one.

Calculate Sigma

The kernels used in the preferred embodiment utilize gaussian distributions to determine the coefficient values and only one dimensional kernels are used to facilitate faster processing. However it is also possible to use two dimensional kernels. Initially, the standard deviation of the distribution, sigma is set to 0.1 and a scaling factor, sigma_scale_factor (SSF), is set to 1.5. sigma is scaled as a geometric series by the scale factor SSF and it controls how quickly the standard deviation increases as the bank of gaussian kernels are calculated. Prior to looping through the process of building the bank of gaussian filters, a second scale factor is determined based upon the grid energy. The grid_energy_sf (GESF) is calculated using:

$$\text{grid\_energy\_sf} = \log\left(\frac{\text{grid\_energy}}{1000.0}\right), \tag{6}$$

where grid_energy is the calculated grid energy from the grid detection processing. If the grid_energy_sf is less than 1.0, it is set to 1.0, and likewise, if the grid_energy_sf is greater than 3.0, it is set to 3.0. Like the SSF, the purpose of the grid_energy_sf is to drive sigma to increase faster so that a larger standard deviation, and thus a flatter kernel is created, resulting in more blur. Thus, the first sigma used in building the first kernel is the product of the initial sigma value, the SSF, and the GESF value. Then for subsequent kernels, sigma is scaled as a geometric series with a scale factor of SSF. In the preferred embodiment, only the grid_energy_sf varies as a function of grid energy. Many types of combinations and variants can be used to control the scaling of the standard deviation which is consistent with the spirit of this invention.

The biggest consideration in the selection of these scale factors is the size of the filter bank being used for the adaptive suppression processing. In the preferred embodiment, 8 filter banks are utilized which results in sigma ranging from 0.1 to 1.71 when the grid_energy_sf is set at 1.0. A sigma value of 0.1 results in a kernel that is an identity kernel—the output equals the input. As sigma increases, the degree of blurring increases. Conceivably, one could have as many filters as one desires, depending upon what the method of adaptively applying the filters is, but such an implementation would be impractical. As one increases the number of filters, the standard deviation scale factors should be decreased, but always greater than 1.0. Once the size of the filter bank (nbank) is known and the scale factors are determined appropriately, the gaussian kernels are built.

Build Filter Bank

The one dimensional form of a gaussian distribution:

$$\text{coefficient}(x) = \frac{1}{\sigma\sqrt{2\pi}} \exp\left(\frac{-x^2}{2\sigma^2}\right), \tag{7}$$

is used to determine the coefficient values, where o is the above calculated standard deviation and x is the kernel index. Due to round-off errors and truncation which can occur by having a small window, a normalization of kernel values is performed to ensure that the sum is 1.0. The σ value is then scaled by the sigma_scale_actor and the process repeated until all kernels are built, as shown in FIG. 9.

Adaptive Suppression

As mentioned earlier, the approach to suppression of the grid is based upon adaptively blurring the image, and the core of the process lies in how the kernel is chosen to be used in convolving a particular pixel in the image. A plurality of methods are presented which describe this process.

Figure 10:
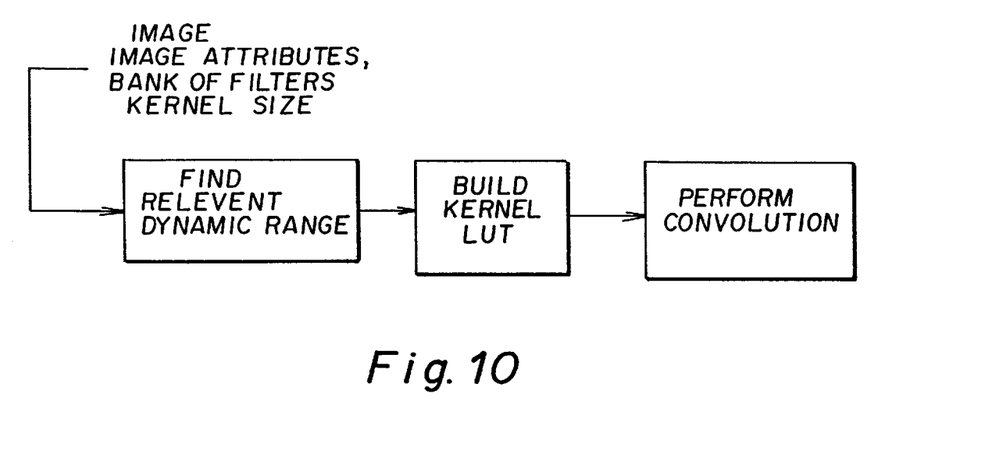
FIG. 10 is a block diagram of adaptive suppression based upon signal level.

Selecting Blur Kernel Based Upon Signal Level In its simplest form, one approach is to select the kernel as a function of signal level (pixel value). FIG. 10 is a block diagram of the stages of this suppression process. As mentioned previously, a filter bank of 8 kernels is used in the preferred embodiment.

Figure 11:
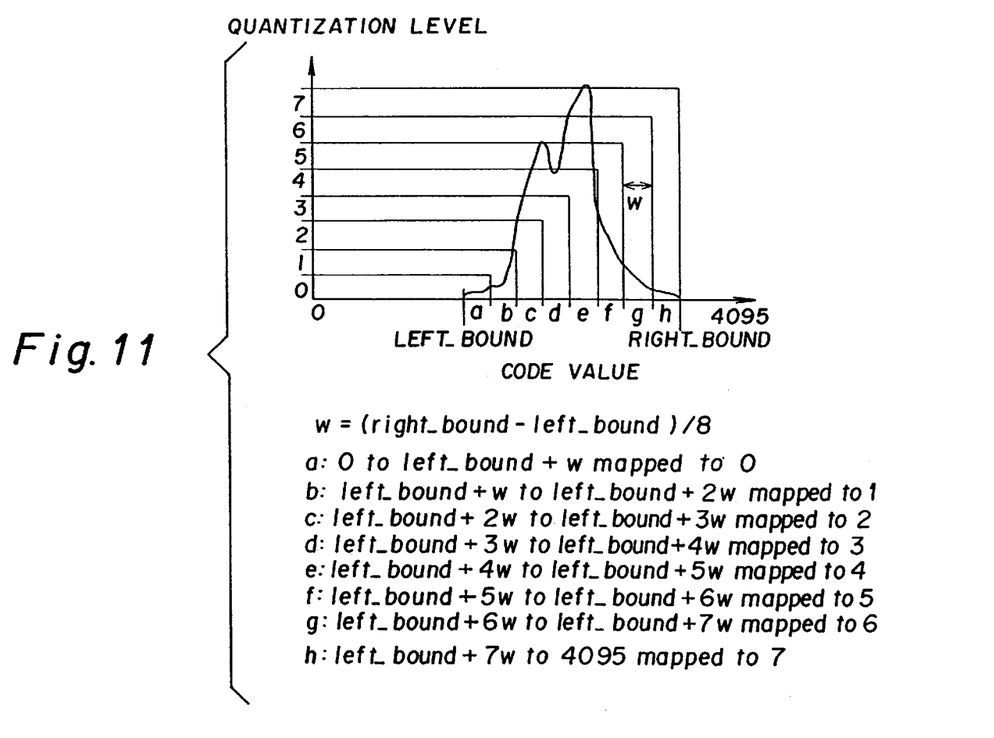
FIG. 11 is an illustration of the method used to construct the kernel look-up table (LUT).

First, the image is analyzed to find the pertinent dynamic range. The method utilized is consistent with the method taught by U.S. Pat. No. 5,633,511, issued May 27, 1997, inventors H. C. Lee et al., specifically, determining the range of code values in the input image. Next, in order to facilitate faster processing, we construct a kernel look up table (LUT) which enables indexing of the appropriate kernel as a function of code value. The range of code values spanned by the dynamic range is quantized to 8 levels and stored as a table such that for any given image code value, a resulting value, 0–7, is provided, corresponding to the index of the kernel in the bank (array) of filters. FIG. 11 demonstrates the construction of the kernel LUT and the quantization technique used.

In finding the usable dynamic range of the image, the left bound and right bound code values are identified. The dynamic range is then divided by the desired number of levels/filters to establish the width of each quantization bin, w. In building our kernel LUT, all code values in the first interval a are mapped to 0; all values in the second interval b are mapped to 1, and so on. Other methods of quantizing the usable dynamic range of the image are also useful, such as perceptual linearization.

Referring again now to FIG. 10, the last step is the convolution process. The methodology of convolution is well known in the art of image processing—see W. K. Pratt, *Digital Image Processing*, 2$^{nd}$ Edition, John Wiley & Sons, Inc., 1991.

Figure 12:
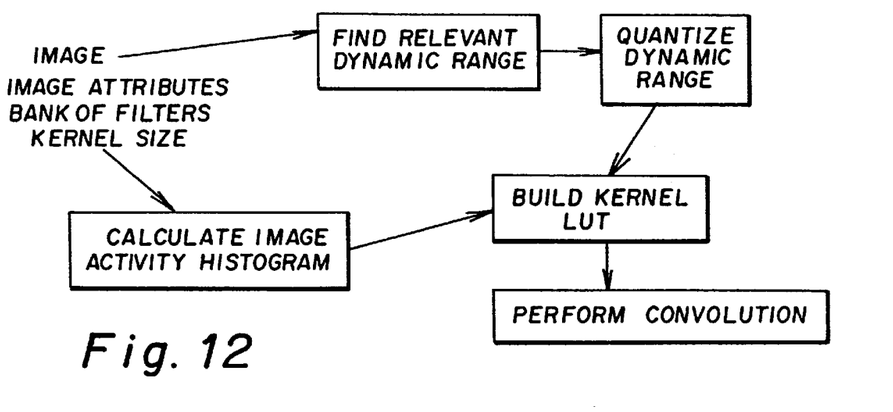
FIG. 12 is a block diagram of adaptive suppression based upon signal level and image activity.

At every pixel in the image, the code value of that pixel is used as an index into the kernel LUT to select the appropriate kernel. Then that kernel is convolved over the corresponding pixel and the result is written to the output file Selecting Kernel Using Both Signal Level And Local Image Activity Measure A second approach to adaptively selecting the blur kernel is to select the kernel as a function of both signal strength and local statistics, for example, a local image activity measure similar to that taught in U.S. Pat. No. 5,633,511. In this approach, joint conditions of signal level and image activity (measured over a local neighborhood) must be combined to select the blur kernel. FIG. 12 demonstrates this approach. The rational is that signal level alone should not drive the selection of the blurring kernel. For example the grid shadows are manifested in the image as slightly lower signal, due to the absorption of x-rays by the lead foil strips, whereas x-rays which passed through unattenuated are slightly higher. Therefore, blur of the pixels which correspond to a grid shadow should be different than the blur of the pixels which correspond to unattenuated x-rays. Secondly, we are using relatively small neighborhoods. If within a neighborhood a large modulation, larger than that expected by noise or the grid, is detected, we should use a low degree of blur to minimize reduction of resolution.

Figure 13:
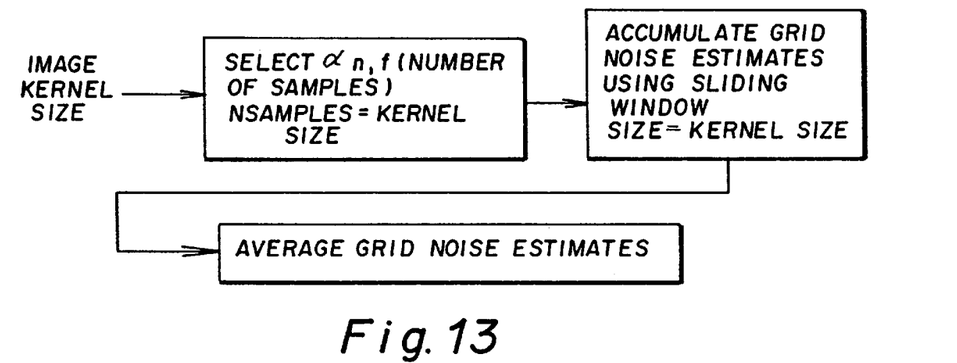
FIG. 13 is a block diagram of constructing the kernel LUT using both signal level and image activity.

In the upper path of the process shown in FIG. 12, finding the relevant dynamic range and quantizing it to the desired number of levels corresponding to the size of the filter bank, is the same as mentioned previously and shown in FIG. 12. The lower path of calculating an image activity histogram creates the second set of criteria for selecting the kernel. First, the noise characteristics of the imaging device must be known a priori. If there is no modulation in an image area, the code values in the immediate neighborhood of a pixel will fluctuate due to noise and grid alone. When there is signal modulation, the neighboring pixels will change with a magnitude much larger than what would be expected from pure noise and grid alone. In order to discern significant modulations not related to the grid, we characterize grid noise as a function of signal level. FIG. 13 describes this process.

For small samples from a normal population, it is known that the range can be used as an unbiased estimator of the standard deviation of the population, that is, $$\sigma = \frac{R}{\alpha_n}, \quad (8)$$

where σ is the standard deviation being estimated, R is the range, and $\alpha_n$ is the expected mean of the range, which is a tabulated value based upon the sample size. In the preferred embodiment, the noise contribution due to the grid is calculated by moving a window the size of the kernel through the image, and at each location, calculating the range and then estimating σ based upon the above equation. This value is stored in an array at the code value corresponding to the pixel at the location being processed. The estimates are then averaged to provide the grid noise estimation function (dependent upon code value). This principle of using the range to estimate the noise is used to significantly reduce processing time.

Using both the noise estimate of the acquisition system and the grid noise estimate, the image activity can be measured. The neighborhood of a given image pixel is evaluated for image activity based upon the number of neighboring pixels which exceed the greater of the two noise thresholds. If the activity is below a predefined floor threshold, the lowest blur kernel is applied. Likewise, if the activity is significantly above a ceiling threshold that corresponds to grid activity, the lowest blur kernel is used. Pixels with activity within the floor and ceiling thresholds maps linearly to increasing degrees of blur, based upon the pixel signal level.

Figure 14:
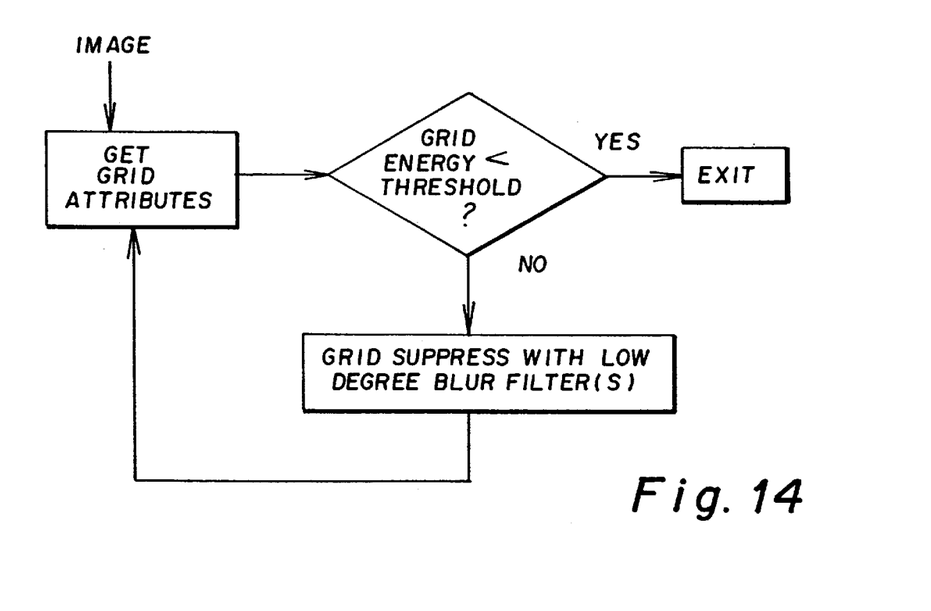
FIG. 14 is a block diagram of adaptive suppression based upon iterative processing.
Figure 15:
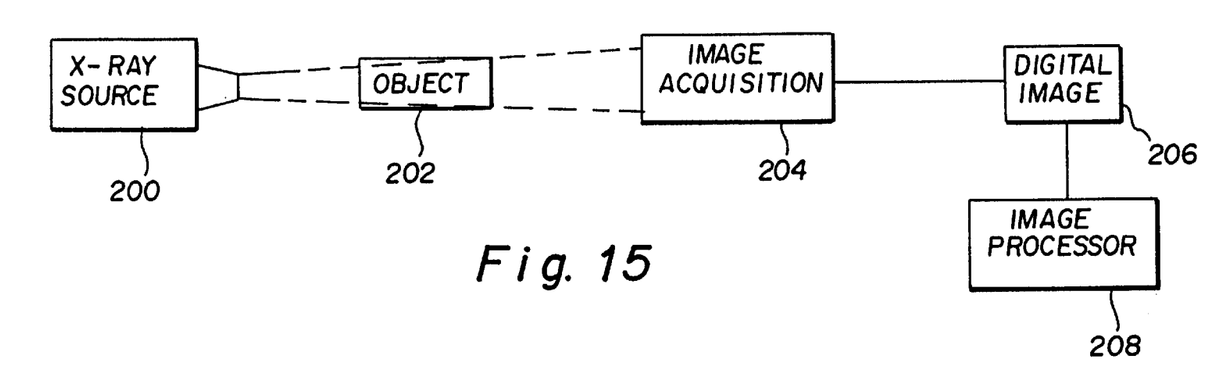
FIG. 15 is a block diagram of a digital radiographic image acquisition system.
Figure 16:
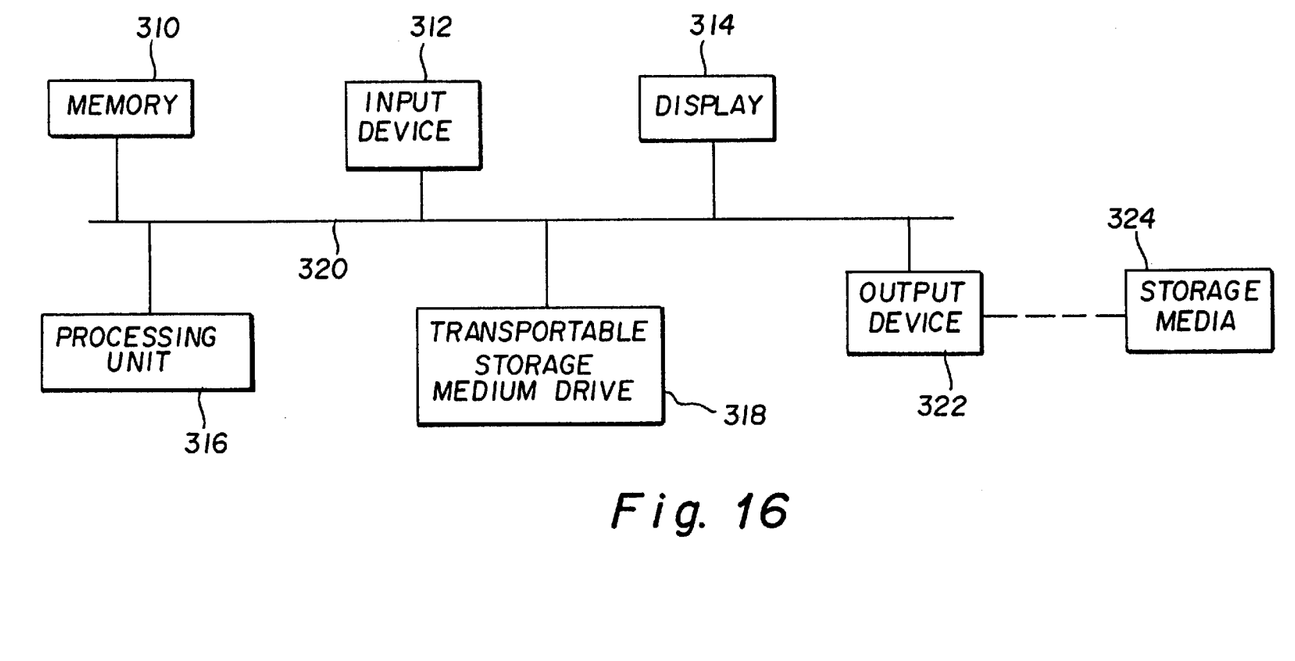
FIG. 16 is a block diagram of a digital processor for carrying out the method of the present invention.

Iterative processing of the image using the Grid Detection process as feedback A third approach to adaptively selecting the blur kernel is to iterate the application of the "low blur" kernel(s) (i.e. results in the least amount of blur to the image) and to stop applying said kernel(s) once the grid energy falls below a predetermined threshold. FIG. 14 describes this process. Through experimental trials, the grid energy threshold which results in indistinguishable aliasing is 750 on an 2500 lines×2000 pixels display with an image addressable area of 2150 lines×2000 pixels. Note that the threshold will be display device dependent as well as software application specific (what image addressable area is used).

Image Re-orientation

As the last stage of processing, if the image was transposed to make the image orthogonal to the orientation of the kernels, the image needs to be transposed back to the original orientation. However if the alternative approach of orientating the kennels to be orthogonal to the grid lines, no further processing is required.

The invention has been described in detail with particular reference to certain preferred embodiments thereof, but it will be understood that variations and modifications can be effected within the spirit and scope of the invention.

PARTS LIST

200 x-ray source
202 object
204 image acquisition system
206 scanner/digitizer
208 image processor
300 digital computer
310 memory
312 input device
314 display
316 central processing unit
318 output device
320 control/data bus
322 transportable storage medium drive
324 transportable storage media

What is claimed is:

1. A digital medical imaging method for improving the presentation of digital projection radiography images comprising the steps of:

providing an input digital radiographic image;

determining a plurality of power spectra from said input digital radiographic image;

identifying all candidate grid frequencies and attributes from said power spectra;

selecting the most likely grid frequencies;

orienting the image for filtering;

calculating the required kernel size as a function of pixel spacing, grid frequency, grid energy and grid half-width full modulation value;

calculating the gaussian sigma value from which to start generating filtering kernels;

building the bank of gaussian filters;

adaptive filtering the image using the bank of gaussian filters; and reorienting the image to original orientation.

2. The method of claim 1 wherein said providing step includes converting an x-ray image stored in a storage phosphor into said input digital radiographic image.

3. The method of claim 1 wherein said providing step includes digitizing a radiographic image on x-ray film to produce said input digital radiographic image.

4. The method of claim 1 wherein said providing step includes converting an x-ray image stored in a flat-panel detector into said input digital radiographic image.

5. The method of claim 1 wherein said power spectra are obtained using FET.

6. The method of claim 1 wherein said determining step obtains said power spectra from the whole input image.

7. The method of claim 1 wherein said determining step obtains said power spectra from a partial region of the input image.

8. The method of claim 7 wherein said partial region includes the most active region of grid lines.

9. The method of claim 8 wherein said most active region of grid lines is obtained based on the local pixel mean.

10. The method of claim 8 wherein said most active region of grid lines is determined using steps which include:

selecting the size of a square window for analysis;

for each location of the square window within the original image, calculating the mean of all the pixels within the square; and choosing the square window location corresponding to the minimum mean for a "white-bone" original image, or the location corresponding to the maximum mean for a "black-bone" original image as the most active region of grid lines.

11. The method of claim 8 wherein said most active region of grid lines is determined using steps which include:

sub-sampling the original image;

selecting the size of a square window for the analysis of the sub-sampled image;

for each location of the square window within the sub-sampled image, calculating the mean of all the pixels within the square;

choosing the square window location corresponding to the minimum mean for a "white-bone" sub-sampled image, or the location corresponding to the maximum mean for a "black-bone" sub-sampled image; and mapping the chosen square window location and the window itself to the original image as the most active region of grid lines.

12. A method of claim 1 wherein said determining step includes:

calculating the 1D power spectra of a selected number of rows and columns of pixels of the original image;

averaging the 1D power spectra of all the selected rows and columns, respectively; and taking the resulting two averaged 1D power spectra as said spectra in claim 1.

13. A method of claim 7 wherein said determining step includes:

calculating the 1D power spectra of a selected number of rows and columns of pixels within said partial region;

averaging the 1D power spectra of all the selected rows and columns, respectively; and taking the resulting two averaged 1D power spectra as said spectra in claim 7.

14. A method of claim 1 wherein said determining step includes:

calculating the 2D power spectrum of the input image;

averaging a selected number of rows and columns of the 2D power spectrum, respectively; and taking the resulting two averaged 1D profile as said spectra in claim 1.

15. A method of claim 7 wherein said determining step includes:

calculating the 2D power spectrum of said partial region;

averaging a selected number of rows and columns of the 2D power spectrum, respectively; and taking the resulting two averaged 1D profile as said spectra in claim 7.

16. The method of claim 1 wherein said identifying step includes the steps of:

optionally smoothing said power spectra;

optionally using morphological opening filter for power spectrum background subtraction;

identifying all the local maxima in said power spectra; and obtaining the attributes of each local maximum, which include frequency, half-width of full maximum, total energy, and peak magnitude.

17. The method of claim 16 wherein said power spectra are two 1D power spectra, one in x direction and the other in y direction.

18. The method of claim 16 wherein said power spectra is actually a 2D power spectrum.

19. The method of claim 1 wherein said selecting step includes the steps of:

eliminating those peaks whose peak magnitude is smaller than a predetermined threshold;

eliminating those peaks whose frequency is lower than a predetermined threshold;

eliminating those peaks whose energy is less than a predetermined threshold, calculating the Figure of Merits (FOMs) of all the rest peaks, which include frequency FOM, energy coherence FOM and total FOM;

eliminating those peaks whose fom_tot is lower than a predetermined threshold; and ranking the rest of the peaks based on their fom_tot.

20. The method of claim 1 wherein said orienting step includes the steps of transposing the image such that grid lines are perpendicular to horizontally oriented 1D kernels.

21. The method of claim 1 wherein said orienting step includes the steps of setting orientation flag such that 1D kernels are oriented perpendicular to grid lines in input image.

22. The method of claim 1 wherein said calculating the required kernel size step includes the steps of calculating the width of a grid shadow, calculating the kernel size, setting the kernel size to the to the half-width full modulation value if said kernel size is smaller, making the kernel size odd, initializing sigma and sigma scale factor; calculating the grid energy scale factor, and setting the first kernel sigma to the product of the initial sigma and the grid energy scale factor.

23. The method of claim 1 wherein said building step includes the iterative steps of using the 1D equation of the gaussian distribution to calculate kernel values, and multiplying sigma by the sigma scale factor until the required number of kernels have been built.

24. The method of claim 1 wherein said adaptive filtering step includes the steps of finding the useful dynamic range, linearly quantizing the dynamic range to build a kernel look-up table (LUT), selecting the kernel from the bank of kernels based on the kernel LUT which is indexed by the code value of the pixel being processed, and convolving said kernel over the region corresponding to the pixel being processed.

25. The method of claim 1 wherein said adaptive filtering step includes the steps of finding the useful dynamic range, quantizing the dynamic range based upon perceptual linearization to build a kernel look-up table (LUT), selecting the kernel from the bank of kernels based on the kernel LUT which is indexed by the code value of the pixel being processed, and convolving said kernel over the region corresponding to the pixel being processed.

26. The method of claim 1 wherein said adaptive filtering step includes the steps of finding the useful dynamic range, quantizing the dynamic range, calculating image activity histogram, using both the code value of the pixel being processed as well as the amount of image activity of said pixel to select kernel LUT, and convolving said kernel over the region corresponding to the pixel being processed.

27. The method of claim 26 wherein said calculating step includes selecting an as the expected mean of the range, accumulating grid noise estimates using a sliding window where at each location of the window, the range is measured and the standard deviation estimated, storing said standard deviations as a function of code value and averaging stored standard deviations.

28. The method of claim 1 wherein said adaptive filter step includes the iterative steps of selecting a kernel of low blurring capability, convolving said filter on entire image, reprocessing the resultant image with the grid detection process including said determining step, said identifying step, and said selecting step, testing if the resulting grid energy is below the required threshold, and repeating said steps until grid energy falls below said threshold.

* * * * *